US012618029B2

(12) United States Patent
Whitton et al.

(10) Patent No.: US 12,618,029 B2
(45) Date of Patent: May 5, 2026

(54) METHOD FOR PRODUCING AGAVE CULTURES FOR TEQUILA

(71) Applicants:Peter Andrew Whitton, Long Beach, CA (US); John R. Munoz, Long Beach, CA (US); Geoffrey Dixon, Long Beach, CA (US)

(72) Inventors: Peter Andrew Whitton, Long Beach, CA (US); John R. Munoz, Long Beach, CA (US); Geoffrey Dixon, Long Beach, CA (US)

(73) Assignee: PHYTOTEQ, INC., Long Beach, CA (US)

( * ) Notice: Subject to any disclaimer, the term of this patent is extended or adjusted under 35 U.S.C. 154(b) by 0 days.

(21) Appl. No.: 18/532,492

(22) Filed: Dec. 7, 2023

(65) Prior Publication Data

US 2024/0141264 A1 May 2, 2024

Related U.S. Application Data

(63) Continuation-in-part of application No. 17/853,163, filed on Jun. 29, 2022, now Pat. No. 11,895,962.

(60) Provisional application No. 63/312,789, filed on Feb. 22, 2022.

(51) Int. Cl.
| | |
|---|---|
| *C12G 3/021* | (2019.01) |
| *C12N 5/00* | (2006.01) |
| *C12N 5/04* | (2006.01) |

(52) U.S. Cl.
CPC ........... *C12G 3/021* (2019.02); *C12N 5/0025* (2013.01); *C12N 5/04* (2013.01)

(58) Field of Classification Search
CPC ..................................................... C12G 3/021
See application file for complete search history.

(56) References Cited

PUBLICATIONS

Arjun and Srinth Rao; Callus induction and Organogensis in Sugarcane (*Saccharum officinarum* L.) var 93v297; International Letters of Natural Sciences; vol. 38; Nov. 3, 2015; pp. 14-22.*

* cited by examiner

*Primary Examiner* — Kent L Bell
(74) *Attorney, Agent, or Firm* — Fulwider Patton LLP

(57) ABSTRACT

A method to expedite the growth of the agave plant by growing the plant tissue from a cell culture in a laboratory utilize incubator cells that are taken from the leaf of an agave plant and grown in a medium containing all the nutrients required for the production of new cells and the maturation of those new cells. The cells are then exposed to photosynthetic active radiation and fed with extra carbon dioxide, causing the cells to undergo photosynthesis and form the sugars that are found in a naturally growing agave plant. These cultivated cells are given an optimum amount of light and carbon dioxide to promote an unexpected and substantially higher growth rate than heretofore achieved.

1 Claim, No Drawings

METHOD FOR PRODUCING AGAVE CULTURES FOR TEQUILA

CROSS-REFERENCES TO RELATED APPLICATIONS

This application a Continuation-In-Part based on U.S. Ser. No. 17/853,163, filed Jun. 29, 2022, which claims priority to U.S. Provisional Patent Application No. 63/312,789, filed Feb. 22, 2022, the contents of which are incorporated herein by reference in their entirety.

BACKGROUND

The present invention is directed to the production of tequila, and more directly to a method of tequila production that provides an alternative to the customary twelve year period required for an agave plant to mature.

Tequila is a distilled spirit commonly made from the Weber blue agave plant. The Weber blue agave plant, or agave tequilana, is a large succulent with long, spiked leaves similar to the aloe vera plant. Within the core of the blue agave plant is a bulb called the piña. To distill tequila, this bulb is baked and juiced, and the juice is fermented with yeast in barrels to make tequila. Tequila is a popular spirit used in many different cocktails, like the Margarita, Paloma, and the Tequila Sunrise.

Traditional tequila is manufactured as follows.

1. Harvest the agave. Modern tequila production begins with the traditional method of harvesting the blue agave plant. A special knife called a coa is used to cut the leaves on the agave plant away from the underground piña bulb.

2. Bake the agave core, or the piña. The piña bulb must be baked in order to extract its fermentable sugars. Traditionally, piñas were baked in pits lined with rocks, but today, they're baked in either clay and brick ovens called hornos, or large stainless steel ovens.

3. Shred the piña and extract the agave juice. After the piñas are baked, they are crushed and shredded to extract the sweet juice inside, which is called mosto. Mosto is extracted in one of two ways: by using an industrial mechanical shredder (the most common modern way), or by the traditional method of using a tahona, a large stone wheel that crushes and juices the piña.

4. Ferment the agave juice, or mosto. Next, the mosto must ferment into ethyl alcohol in order to become a spirit. The mosto is combined with yeast and water in large fermentation tanks. This process uses either large stainless steel tanks, or large wooden barrels.

5. Distill the fermented mosto. The agave juices are then distilled, which purifies the liquid and concentrates the alcohol in the mixture. Tequila is typically distilled twice. The first distillation produces a cloudy liquid called the ordinario. The second distillation produces the clear silver tequila, which is then ready to be aged and bottled.

6. Age the tequila. All tequila is aged for at least 14 to 21 days. Silver or blanco tequila is aged for the minimum time. Aged tequila comes in three types: reposado ("rested," aged for two months to one year), añejo ("aged," aged for one to three years), and extra añejo (aged for over three years). To produce a more aged tequila, the distilled blanco is put into aged oak barrels, which gives the tequila a golden color. There is also a fifth kind of tequila called joven ("young") or oro ("gold"), which is a mix of silver tequila and reposado tequila.

The Mexican government strictly regulates the production of the agave plant, which by law is limited to certain states of Mexico including Jalisco, Nayarit, Guanajuato, Michoacán, and Tamaulipas. In addition, it takes twelve years for the agave plant to grow large enough to be cultivated for the production of tequila. The combination of these two limitations, along with the boom in tequila sales and the influx of new tequila makers has led to a severe shortage of the agave plant. Today the production of agave falls far short of demand, and the situation is expect to get worse in the near future. Of these issues, the twelve year incubation period of the plant has the biggest effect in the shortage of the agave plant. Heretofore, the only way to obtain the necessary sugars and ingredients was to wait the twelve years for the plant to mature.

SUMMARY OF THE INVENTION

The present invention is a method to expedite the growth of the agave plant by growing the plant tissue from a cell culture in a laboratory. A novel method has been developed that permits the cells to grow quickly without ever having to be part of the plant. Incubator cells are taken from the leaf of an agave plant and grown in a medium containing all the nutrients required for the production of new cells and the maturation of those new cells. The cells are then exposed to photosynthetic active radiation and fed with extra carbon dioxide, causing the cells to undergo photosynthesis and form the sugars that are found in a naturally growing agave plant. These cultivated cells are given an optimum amount of light and carbon dioxide to promote an unexpected and substantially higher growth rate than heretofore achieved.

Once the culture has matured and sufficient sugars have been produced, e.g., the media solution is around 8% sugar, then yeast is added and the entire media/cell solution is allowed to ferment until the sugar is completely converted to ethanol. In one preferred embodiment, citric acid is added to the media solution in order to reduce the pH to a range of between 3.5 and 4.5. This reduction in pH facilitates the process of photosynthesis as follows: the energy required in the light reaction of photosynthesis is used to split the hydrogen ion from a water molecule in order to turn NADP into NADPH; and lowering the pH in which the cells can still survive leads to more hydrogen ions available to the chloroplasts and thereby reduces the amount of light energy required to split the water molecule.

In another embodiment the pH is buffered at 5.5 to allow better formation of fructans (simple starches). These starches form as suspended solids that can be removed from the media upon formation. To capture the fructans the media is recirculated through a transverse flow filter with a pore size of approximately 0.32 micron. The starches suspended in the media pass through this membrane, whereupon the cells are returned to the bioreactor. The suspended starches are then removed from the liquid media via filtration or centrifugation and the media can then be sterile filtered and added back to the bioreactor.

The ethanol is then distilled off, as well as the other aromatic compounds produced in order to make a tequila. The process reduces the twelve year waiting period to approximately twenty four weeks, dramatically increasing production and efficiency of the process.

3

DETAILED DESCRIPTION OF THE PREFERRED EMBODIMENTS

The process by which tequila is derived according to the present invention is broken down into four phases set forth below. It will be understood that there are variations of the ingredients and condition that will still result in the finished product, and the following description should be considered the inventor's best mode for carrying out the invention, but does not exclude the aforementioned variations of which a person of ordinary skill would 0.5.5 recognize.

Initiation of Callus Cultures from Agave: Preparation of Callus Induction Media

In another embodiment the cells may be taken from sugar cane leaf to produce rum, from barley or rye to produce whiskey, or from other suitable plants to produce beers, wines or other spirits.

A solution is prepared with distilled water to 100%, into which sucrose (3%), naphthalene acetic acid (NAA, 1%) of 0.004% stock solution, and Murashige and Skoog basal powdered medium (0.44%) is added.

A callus induction media is prepared using the Murashige and Skoog (MS) media obtained from Sigma Aldrich®, with 3% sucrose and 1% naphthalene acetic acid (from a concentrated stock solution of 0.004% w/v). The prepared media is preferably adjusted to a pH of approximately 5.75 and solidified with 0.2% phytagel. The media is then autoclaved for twenty minutes at approximately 121° C. and poured out into sterile plastic plant tissue culture dishes.

Initiation of Callus Cultures from Agave: Sterilization of Plant Tissue

Leaf tissue of Agave is sterilized by immersing it in a 70% ethanol solution for two minutes, followed by immersion in a 10% bleach solution for ten minutes. The Agave is washed multiple times with sterile (autoclaved) distilled water and aseptically cut into disk shapes within a sterile laminar flow cabinet. The Agave slices are placed onto the prepared plates containing the callus induction media and the plates are subsequently sealed with a film such as a Nescofilm™. The sealed plates are then placed into a darkened enclosure with an air temperature of approximately 27° C. Under these conditions, a callus formation will begin to appear after about thirty days.

Media Preparation for Established Cultures

In the third phase of the invention, the callus formations are introduced into a medium for accelerated growth. The previous media from step one is repeated (Distilled water, sucrose, Murashige and Skoog basal powder, and NAA), supplemented with a 0.01% vitamin stock solution comprising 0.05% pyridoxalhydrochlorid, 0.10% thiamine dichloride and 0.05% g nicotinic acid. Mixing the 3% sucrose, 0.44% MS powder, 1% NAA stock and 0.01% vitamin stock in the 100% distilled water gives the base medium. Using a magnetic stirrer, the ingredients are mixed until all dry components are dissolved, and then the medium is adjusted using first a 1 M solution of NaOH and then a 0.1M solution of NaOH to obtain a pH of 5.75. Using 250 ml conical flasks, 50 ml of media are introduced, and the necks of the flasks are sealed with foil. Each sealed flask is sterilized in an autoclave at 121° C. and 103 kPa for approximately 25 minutes. Thereafter, the flasks are placed into a laminar flow cabinet and then allow to cool to an ambient temperature.

Inoculation and Subculture of Established Cultures

The final stage of the process is the inoculation and development of subcultures from the established cultures. Initially, the laminar flow cabinet and the instruments are sterilized with a solution of 70% ethanol, and in the case of the instruments (tweezers, spatulas, etc.) heated until glowing red before allowing to cool inside the sterilized laminar flow cabinet. The foil is removed from each prepared media flask within the sterilized laminar flow cabinet, and using sterilized tweezers, the thumbnail sized pieces of friable callus are removed from the plant tissue. These friable callus are broken up into finely dispersed cells and added to the flask. In a preferred embodiment, approximately 5 grams of tissue is added to 50 ml of media (10% w/v). Once the callus is added to the flask, the neck of the flask is flamed and then covered with a sterile sheet of foil. The sealed flask is placed on a shaker at 120 rpm in a dark room having an ambient temperature of approximately 27° C. The flasks are left until a thick, dispersed cell suspension culture is observed (approximately 2 weeks).

Subculture

After this incubation period, the foil is removed from prepared media flask within the sterilized laminar flow cabinet, and the foil from flask containing dispersed cell suspension cultures (produced by initial inoculation) is also removed. Using a sterilized wide spatula with holes, the cells are scoop out and added to the fresh media. In a preferred embodiment, approximately 5 grams of tissue is added to 50 ml of media. Citric acid may be added to the media to lower the pH to a range of between 3.5 and 4.5, with a more preferred pH of 4.0. The neck of the flask is flamed and covered with a sterile sheet of foil. Then the flask is placed on a shaker at 120 rpm, in a light room heated to 27° C. After 14 days, the cell suspension culture can be used for further subcultures or the cells harvested and frozen dry.

Establishment of Intermediate Cultures

The final stage of the process is the preparation of 20 liter culture bags. This begins with the formation of the medium using the 3% sucrose, 0.44% MS powder, 1% NAA stock and 0.01% vitamin stock in the 100% distilled water. Using a magnetic stirrer the ingredients are mixed until all dry components dissolved, and then the pH is adjusted using the 1 M and 0.1 M NaOH solutions to yield a pH of 5.75. Using three 20 L (nominal) sterile vessels, add to each one bag of media aseptically using the a peristaltic pump, tubing and 0.2 micron sterile filter. This transfer is to be carried out within the sterile laminar flow cabinet. Using sterile 50 ml syringes, 200 ml of cells are transferred from the 250 ml flask to the media in the bag using the addition port on the vessel. The mixture is incubated in the laboratory for 4 weeks, and then the culture vessel is placed in PAR light so that there is 1 W of light output per liter of culture liquid. Air is added through a diffuser into the liquid so that the air flow is 200 ml/minute. Carbon Dioxide is added through the diffuser into the liquid so that the $CO_2$ flow is 50 ml/minute. This mixture is incubated for approximately six weeks until the total sugars when measured by dry weight equals six percent (6%) or above. At this point, the light and all gas flow are turned off and brewer's yeast is added to the liquid. This is followed by a fermentation period of approximately 5 to 10 days. Once fermented, the produced ethanol can be removed by distillation, where the distillate may have water added to reduce the ethanol content to that which is expected from a tequila.

The foregoing process represents the inventor's best mode of carrying out the invention, but a person of ordinary skill in the art will recognize that there are modifications and substitutions to the process that will still lead to a tequila in far less time that the normal growth development of the Agave plant. The invention is intended to include all such modifications and substitutions that would be apparent to those skilled in the art, and nothing herein should be interpreted as excluding any variation of the method unless expressly so stated. Rather, the invention is to be considered all variations and substitutions covered by the claims using their ordinary and customary meanings consistent with, but not exclusionary to, the foregoing descriptions.

We claim:

1. A method for cultivating sugar cells, comprising:

(a) preparing a callus induction media including a sugar, naphthalene acetic acid, and water;

(b) placing sugar cane leaf cells into the callus induction media to incubate a callus formation;

(c) establishing a mixture by placing the callus formation into an accelerator media comprising a sugar, naphthalene acetic acid, and water;

(d) heating the mixture of (c);

(e) using cultures obtained from the mixture to cultivate subcultures from the accelerator media, and supplementing the subcultures in the accelerator media with an acid; and (f) adding carbon dioxide and yeast;

wherein sugar cells reproduce and are cultivated from the accelerator media.

\* \* \* \* \*